United States Patent [19]

Mayer

[11] Patent Number: 5,165,728

[45] Date of Patent: Nov. 24, 1992

[54] NIPPLE INTENDED TO COOPERATE WITH MULTIPLE COUPLING COMPONENTS

[75] Inventor: Georg Mayer, Hechingen-Boll, Fed. Rep. of Germany

[73] Assignee: Gambro Dialysatoren GmbH & Co. KG, Fed. Rep. of Germany

[21] Appl. No.: 643,421

[22] Filed: Jan. 22, 1991

[30] Foreign Application Priority Data

Feb. 15, 1990 [SE] Sweden .................................. 9000541

[51] Int. Cl.[5] .............................................. F16L 37/00
[52] U.S. Cl. ........................................ 285/12; 285/316
[58] Field of Search .................. 285/12, 316, 241, 277

[56] References Cited

U.S. PATENT DOCUMENTS

| | | |
|---|---|---|
| 2,518,542 | 8/1950 | Hansen . |
| 3,351,362 | 11/1967 | Hansen . |
| 3,473,782 | 10/1969 | Gessic ..................... 285/12 |
| 3,863,958 | 2/1975 | Todd ...................... 285/12 |
| 4,198,080 | 4/1980 | Carpenter . |
| 4,582,347 | 4/1986 | Wilcox et al. ............. 285/12 |
| 4,595,217 | 6/1986 | Siegel ..................... 285/12 |
| 4,798,404 | 1/1989 | Iyanicki ................... 285/12 |

*Primary Examiner*—Eric K. Nicholson
*Attorney, Agent, or Firm*—Lerner, David, Littenberg, Krumholz & Mentlik

[57] ABSTRACT

Nipples for use in coupling various secondary coupling components including so-called Hansen couplings are disclosed in which the nipple includes a longitudinally extending cylinder which includes an outer recess on its outer surface which is adapted for engagement with a Hansen-type secondary coupling component including a locking element for engaging the outer recess, and in which the nipple includes threads located between the outer recess and the outer end of the longitudinally extending cylinder, which are adapted for engagement with a secondary coupling component including corresponding threads thereon. The disclosed nipples are intended to be used in order to couple dialyzer or similar diffusion and/or filtration devices to different tube systems which can include coupling components which are intended for throw-away use and/or for multiple usage.

25 Claims, 6 Drawing Sheets

Fig. 3A
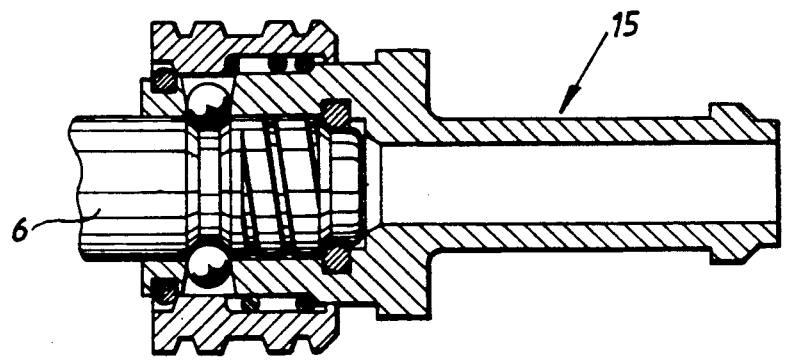
Fig. 3B
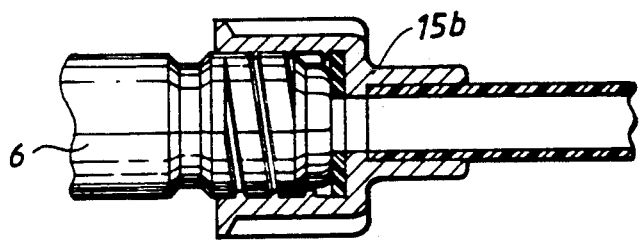
Fig. 3C
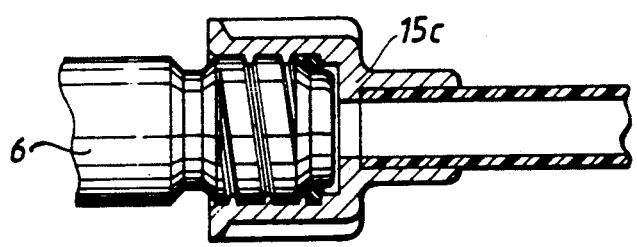
Fig. 3D
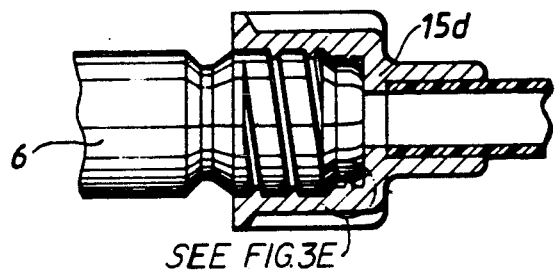
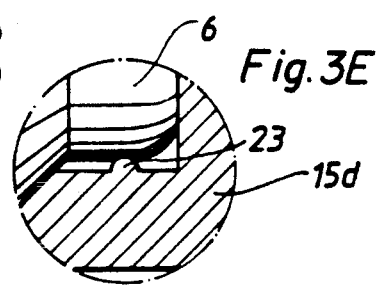
Fig. 3E

NIPPLE INTENDED TO COOPERATE WITH MULTIPLE COUPLING COMPONENTS

FIELD OF THE INVENTION

The present invention relates to a nipple, and in particular, a nipple which is intended to form part of a so-called Hansen coupling. More particularly, the present invention relates to nipples intended for use with Hansen couplings in which one coupling component comprises the nipple which includes at least one recess on its outer peripheral surface while the other coupling component has a sleeve-like portion, which is capable of being telescopically pushed over the nipple, and which includes a locking means, such as balls, which are engaged in the recess on the outer surface of the nipple.

More particularly, the present invention relates to nipples which are intended to form part of a dialyzer or similar diffusion and/or filtration device. Still more particularly, the present invention relates to such nipples which are intended for use in such apparatus so as to render it possible to couple same to different tube systems, which can include coupling components intended either for throw-away use or which are intended for multiple utilization. Alternatively, the present invention is also directed to such nipples which can form part of a tube coupling for the coupling together of two tubular components.

BACKGROUND OF THE INVENTION

There are a number of different examples of Hansen couplings, such as those shown in U.S. Pat. Nos. 2,518,542; 3,351,362 and 4,198,080. As is evident from the sheer number of these patents, this type of coupling has been in use for a rather long period of time. These Hansen-type couplings consist, on the one side, of a nipple, and on the other side of a sleeve-like portion which is capable of being telescopically pushed over the nipple. The sleeve-like portion of the coupling exists in various forms including both simple and somewhat more complicated variants. They each have the common disadvantage, however, that they are too expensive to be used simply for throw-away use. The other coupling component, i.e., the nipples themselves, may, of example, form part of a dialyzer, and thus be coupled normally by means of conventional Hansen couplings to tubes originating from a conventional dialysis monitor. If it is desired to use this same housing provided with such nipples in connection with hemofiltration, for example, the nipples must then be coupled to a tube set which is intended for throw-away use. Because of the concomitant high cost, such an arrangement cannot comprise conventional Hansen couplings, but must instead make use of simpler couplings, such as simple threaded plastic components and the like.

SUMMARY OF THE INVENTION

It is therefore an object of the present invention to provide a nipple which, while being adapted to cooperate with so-called Hansen-type couplings, can also be used with other coupling components, such as simple threaded plastic components and the like.

In accordance with the present invention, these and other objects have now been realized by the invention of a nipple which can be used for coupling to a plurality of secondary coupling components, the nipple comprising a longitudinally extending hollow cylindrical member having an outer surface, an inner surface, an inner end, and an outer end, with the outer surface of the longitudinally extending hollow cylindrical member including an outer recess adapted for engagement with a Hansen-type secondary coupling component, including locking means for engaging the outer recess, and the nipple further including thread means located between the outer recess and the outer end of the longitudinally extending hollow cylindrical member, the thread means being adapted for engagement with a threaded secondary coupling component including corresponding threads thereon.

The nipple in accordance with this invention is thus adapted so that it can form part of a so-called Hansen coupling, and thus includes a nipple with one or more recesses on its outer peripheral surface so that it can couple with a secondary coupling component having a sleeve-like part capable of being telescopically pushed over the nipple and which is provided on its inside with locking means such as balls which can engage in the recess or recesses of the nipple, and which is further characterized by a thread arranged either on the inside or the outside of the nipple and situated between the outer end of the nipple and the recess or recesses, and which is suitable for coupling together with other coupling components provided with a matching thread therefor. In order that the nipple of the present invention can adapt to be fit with a majority of standard Hansen-type couplings, the recess on the outer surface of the nipple preferably constitutes a circular groove around the entire periphery of the nipple, the groove being separated from the outer end of the nipple by a raised cylindrical portion. This groove, however, can be replaced by one or more recesses of different shapes and sizes.

In accordance with one embodiment of the nipple of the present invention, the thread means are located on the outer surface of the longitudinally extending hollow cylindrical member.

In accordance with another embodiment of the nipple of the present invention, the thread means are located on the inner surface of the longitudinally extending hollow cylindrical member.

In a preferred embodiment in which the thread means are located on the outer surface of the longitudinally extending hollow cylindrical member, that member also includes a raised cylindrical portion located between the annular groove and the outer end of the longitudinally extending hollow cylindrical member. In a preferred embodiment, the raised cylindrical portion is adapted to serve as a sealing surface with respect to at least one of the plurality of secondary coupling components. Preferably, the nipple includes a chamfered surface located between the raised cylindrical portion and the outer end of the longitudinally extending hollow cylindrical member, the chamfered surface being adapted to act as a seal with respect to at least one of the plurality of secondary coupling components.

In accordance with this invention, in order to achieve a relatively good seal, either the raised cylindrical portion itself can be adapted to serve as a sealing surface upon coupling, or it can be finished off on the outside by an inwardly chamfered sealing surface which is adapted to either seal against the other coupling component or against a packing or other seal provided therein.

In accordance with another embodiment of the nipple of the present invention, the raised cylindrical portion has a first diameter, and the outer end of the longitudinally extending hollow cylindrical member includes an end cylindrical portion having a second diameter, with the second diameter being less than the first diameter.

In accordance with one embodiment of the nipple of the present invention in which the thread means are located on the outer surface of the longitudinally extending hollow cylindrical member, the thread means are preferably dimensioned such that the threads are not engageable with the locking means of the Hansen-type secondary coupling component. This is, the nipple is preferably designed such that the locking means in the Hansen-type secondary coupling component to which it is to be coupled cannot fall down in locking position into the thread, but can only do so with the recess or recesses specifically adapted therefor. In this manner, the advantages of the design set forth in the aforementioned U.S. Pat. No. 4,198,080 can be obtained with its ridges extending axially to the nipple, i.e., so that a reduced build-up of material in the otherwise thickened portion of the nipple can be utilized without any risk of an incorrect locking position being created.

In accordance with another embodiment of the nipple of the present invention, the thread means has a predetermined depth so as to provide an internal thread diameter for the thread means, and the second diameter of the end cylindrical portion is less than that internal thread diameter.

In another embodiment, a particularly good seal is obtained if the nipple includes the aforementioned end cylindrical portion which is narrower than the raised cylindrical portion, and these two portions are further separated by a chamfered surface whose original height is preferably slightly higher than the depth of the threads.

In accordance with one embodiment of the nipple of the present invention in which the thread means are located on the inner surface of the longitudinally extending hollow cylindrical member, the thread means comprise a plurality of axially extending bead components which are adapted to interact with an internal valve in the Hansen-type secondary coupling component. Preferably, this plurality of bead components comprise three such bead components evenly distributed about the inner surface of the longitudinally extending hollow cylindrical member. In this embodiment, the threads are thus arranged in a number of axially extending ridges or beads which are inwardly directed and which, in connection with a standard Hansen coupling, are intended to open an inner valve in that other coupling component. An acceptable thread can be achieved if these ridges or grooves are three in number and are evenly distributed about the periphery of the inner, otherwise cylindrical surface of the nipple.

In accordance with one embodiment of the nipple of the present invention, the end cylindrical portion having a reduced diameter is adapted to sealingly cooperate with a sealing bead directed inwardly from the second coupling component. Alternatively, however, the nipple can itself be provided with a sealing bead, which is adapted to seal against a smooth cylindrical sealing surface facing inwardly from the other coupling component.

The seal can be further improved if the threads are adapted to extend in towards the recess or recesses but without reaching same. Thus, in a preferred embodiment, these thread means are separated from the outer recess on the outer surface of the longitudinally extending hollow cylindrical member.

In accordance with another embodiment of the present invention, apparatus for diffusion or filtration are provided including at least one nipple, the nipple being adapted for use in coupling the apparatus to a plurality of secondary coupling components, and the nipple including a longitudinally extending hollow cylindrical member having an inner surface, an outer surface, an inner end and an outer end, and the outer surface of the longitudinally extending hollow cylindrical member including an outer recess adapted for engagement with a Hansen-type secondary coupling component including locking means for engaging said outer recess, said nipple including thread means located between the recess and the outer end of the longitudinally extending hollow cylindrical member and being adapted for engagement with a threaded secondary coupling component including corresponding threads thereon. In this manner, the present invention relates to application of such a nipple in a manner such that the nipple can be used to couple a dialyzer or similar diffusion and/or filtration device to different tube systems which can include coupling components intended either for throw-away use or of the type which are intended for multiple use.

BRIEF DESCRIPTION OF THE DRAWINGS

The following detailed description of the invention can be more fully appreciated with reference to the following Figures, in which:

FIG. 3A is a side, elevational, partially sectional view of the coupling component of FIG. 2A coupled to a nipple in accordance with the present invention;

FIG. 3B is a side, elevational, partially sectional view of the coupling component of FIG. 2B coupled to a nipple in accordance with the present invention;

FIG. 3C is a side, elevational, partially sectional view of the coupling component of FIG. 2C coupled to a nipple in accordance with the present invention;

FIG. 3D is a side, elevational, sectional view of the coupling component of FIG. 2D coupled to a nipple in accordance with the present invention;

FIG. 3E is an enlarged view of a portion of FIG. 3D;

DETAILED DESCRIPTION

Figure 1:
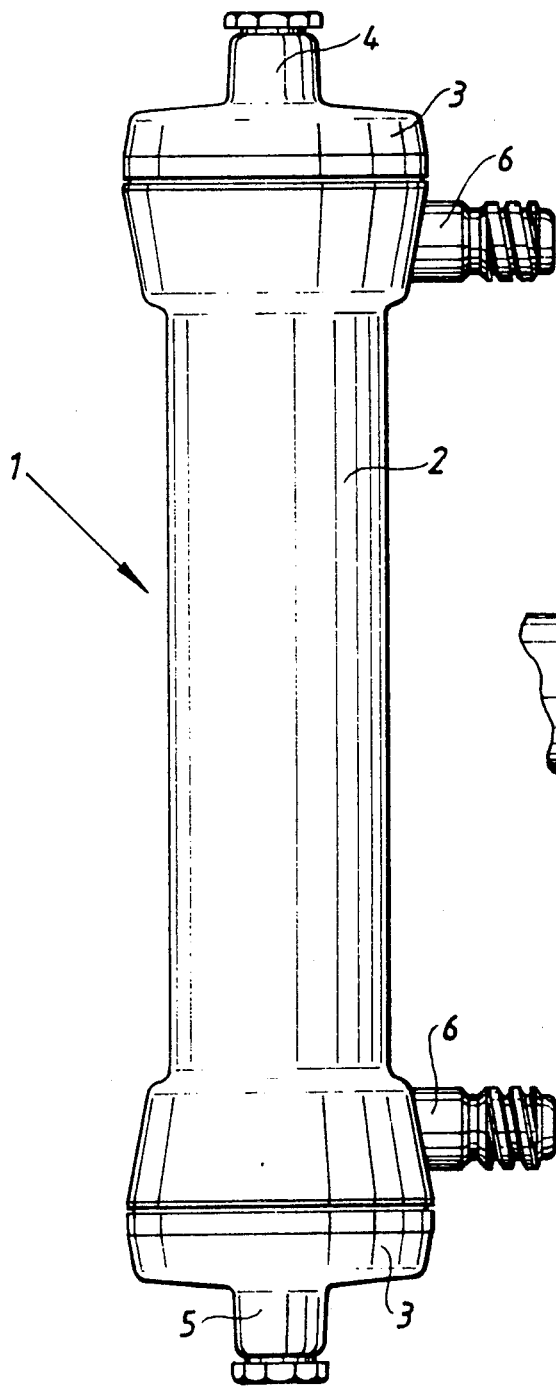
FIG. 1 is a side, elevational view of a dialyzer or other such diffusion and/or filtration device modified with two nipples according to the present invention.
Figure 4:
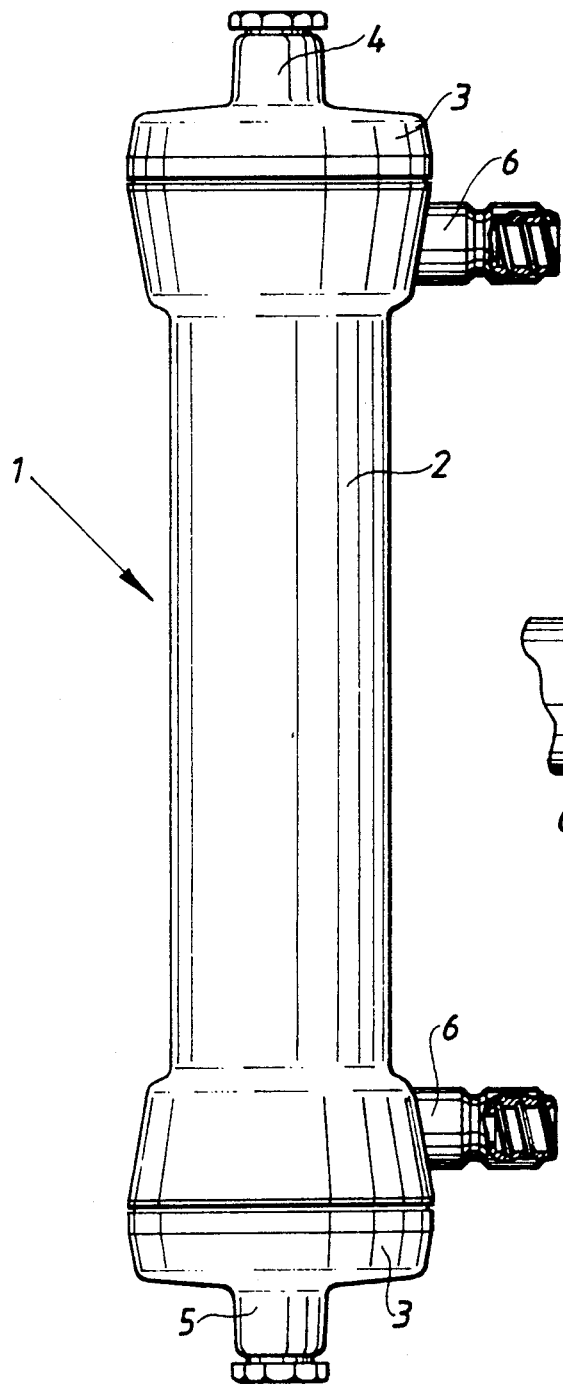
FIG. 4 is a side, elevational view of a dialyzer or other diffusion and/or filtration device modified with two nipples in accordance with another embodiment of the present invention including an internal thread.

Referring to the Figures, in which like reference numerals refer to like portions thereof, it is first noted that the specific designs shown in FIGS. 1 and 4 will be referred to, for purposes of clarity, simply as dialyzers.

FIG. 1 shows a dialyzer 1 consisting of a casing 2 having two end closure parts 3, and with an inlet 4 and an outlet 5 for the dialyzed fluid. If the design shown in FIG. 1 is used solely for dialysis, dialysis fluid is supplied and withdrawn through two nipples 6.

Figure 1A:
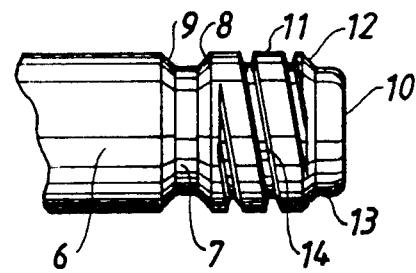
FIG. 1a is a side, elevational, partial, enlarged view of one of the nipples shown in FIG. 1.

Nipple 6 is shown on a larger scale in FIG. 1a. Nipple 6 is provided about its periphery with a recess 7 having chamfered walls 8 and 9. The outer end of the nipple is designated by reference numeral 10. Between the groove 7 and the outer end 10 there is a raised cylindrical portion 11, as is customary on nipples which are used for conventional Hansen couplings. This is finished off towards the outer end 10 thereof by a chamfered surface 12, which is separated from the outer end 10 by a lowered or reduced diameter cylindrical portion 13. The nipple 6 is provided with a thread 14 on the raised cylindrical portion 11.

Figure 2A:
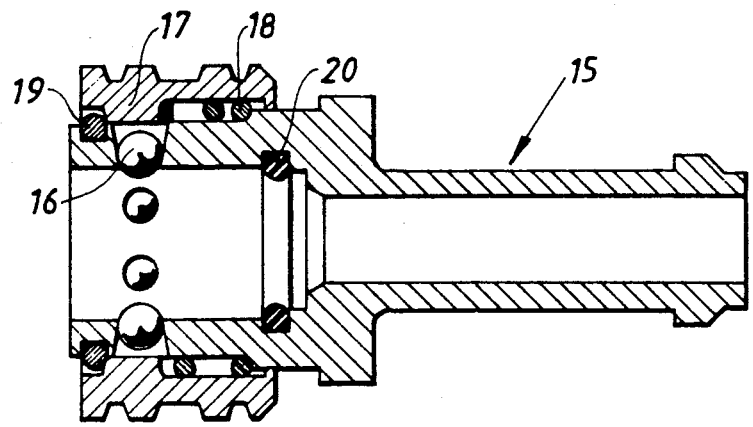
FIG. 2A is a side, elevational, sectional view of a Hansen-type coupling component for coupling to a nipple in accordance with the present invention.

In FIG. 2A there is shown a coupling component 15, which is standard for a conventional Hansen coupling, and is adapted to be coupled to the nipple 6 shown in FIG. 1A. The coupling component 15 is provided with locking means 16 acting inwardly, in this case being balls which are intended to engage in the groove 7 in the nipple 6 upon coupling. The balls 16 are controlled in a conventional manner, by means of guide ring 17 arranged between a spring 18 and a lock ring 19. The coupling component shown also comprises a packing 20.

Figure 2B:
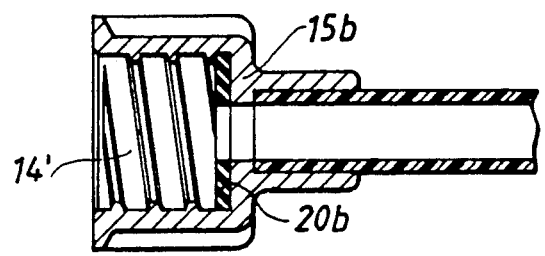
FIG. 2B is a side, elevational, sectional view of another secondary coupling component for coupling to a nipple in accordance with the present invention.
Figure 2C:
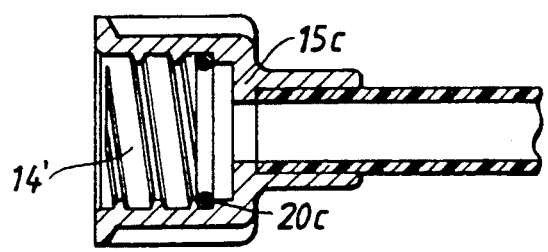
FIG. 2C is a side, elevational, sectional view of another secondary coupling component for coupling to a nipple in accordance with the present invention.
Figure 2D:
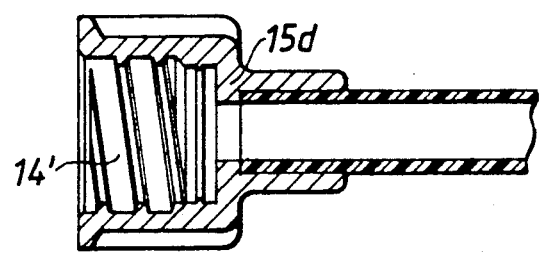
FIG. 2D is a side, elevational, sectional view of another secondary coupling component for coupling to a nipple in accordance with the present invention.

In FIGS. 2B, 2C and 2D, thee are shown three further coupling components 15b, 15c and 15d, respectively, each of which is provided with an internal thread 14' matching thread 14. The coupling components according to FIGS. 2B and 2C are also provided with a packing, 20b and 20c, respectively.

As is evident from FIGS. 3A through 3D, each of the coupling components in accordance with FIGS. 2A through 2D fit the nipple 6, and can be sealingly coupled thereto. The specific seal in accordance with the design according to FIG. 3D is brought about by means of a sealing bead 23, which is specifically shown in the enlarged circular section thereof shown in this Figure.

Figure 4A:
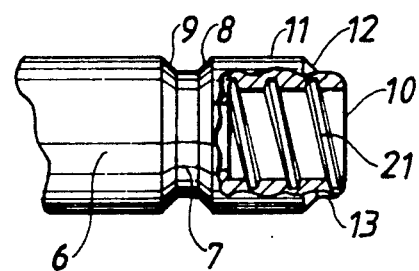
FIG. 4A is a side, elevational, partial, enlarged view of one of the nipples shown in FIG. 4.
Figure 5A:
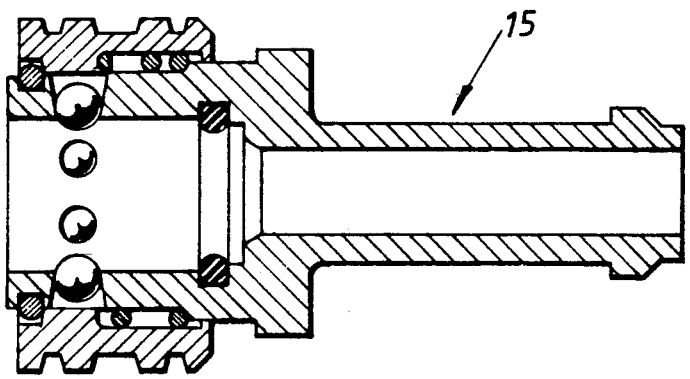
FIG. 5A is a side, elevational, sectional view of a Hansen-type coupling component for coupling to a nipple in accordance with the present invention.
Figure 5B:
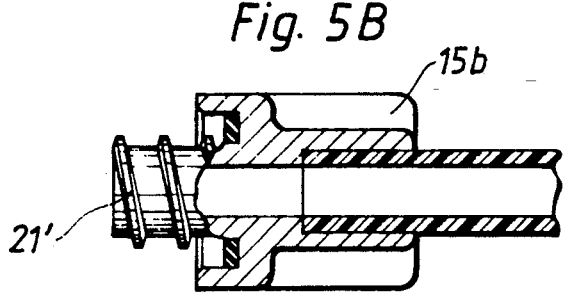
FIG. 5B is a side, elevational, partial, sectional view of another secondary coupling component for coupling to a nipple in accordance with the present invention.
Figure 5C:
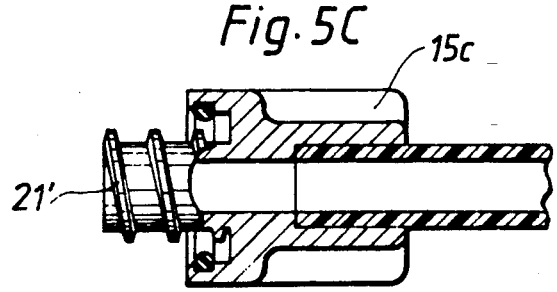
FIG. 5C is a side, elevational, partially sectional view of another secondary coupling component for coupling to a nipple in accordance with the present invention.
Figure 5D:
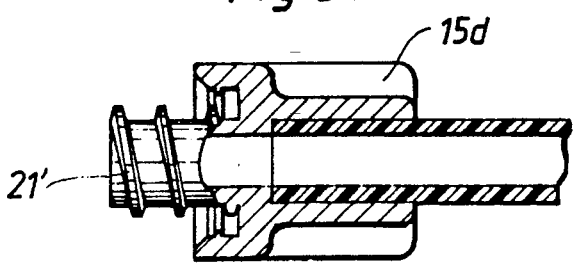
FIG. 5D is a side, elevational, partially sectional view of another coupling component for coupling to a nipple in accordance with the present invention.
Figure 6A:
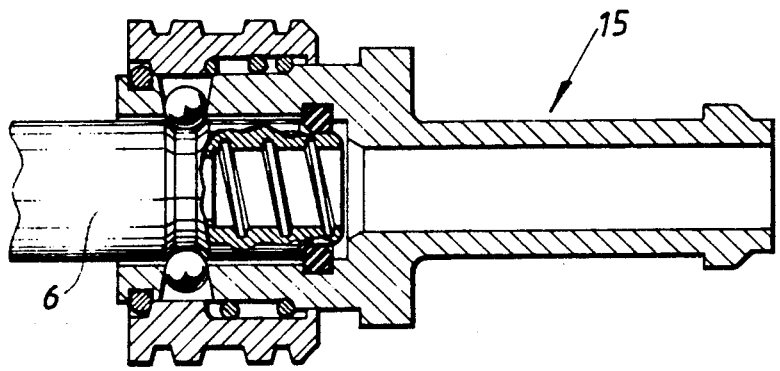
FIG. 6A is a side, elevational, partially sectional view of the coupling component of FIG. 5A coupled to a nipple in accordance with the present invention.
Figure 6B:
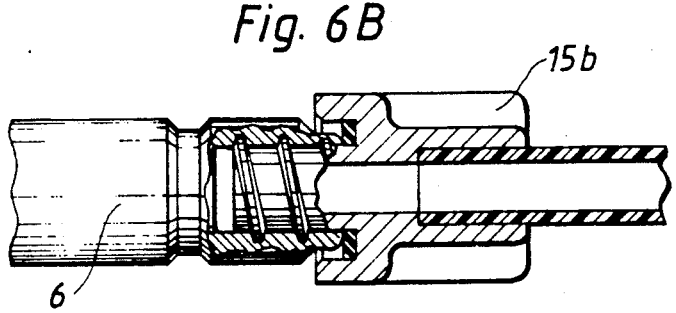
FIG. 6B is a side, elevational, partially sectional view of the coupling component of FIG. 5B coupled to a nipple in accordance with the present invention.
Figure 6C:
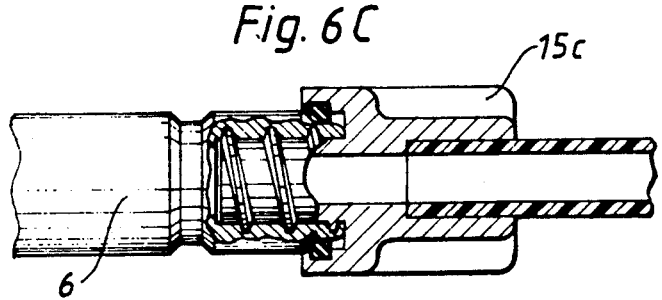
FIG. 6C is a side, elevational, partially sectional view of the coupling component of FIG. 5C coupled to a nipple in accordance with the present invention.
Figure 6D:
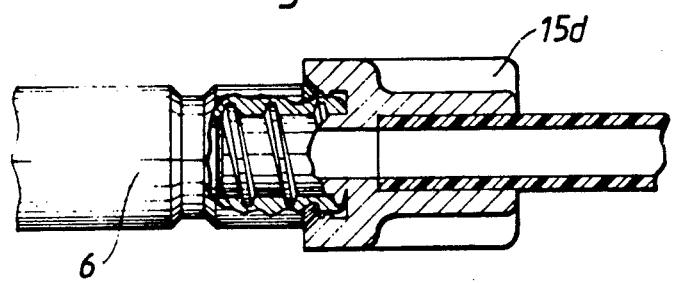
FIG. 6D is a side, elevational, partially sectional view of the coupling component of FIG. 5D coupled to a nipple in accordance with the present invention.
Figure 7:
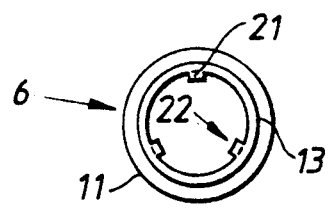
FIG. 7 is an end elevational view of another embodiment of a nipple in accordance with the present invention.

The designs according to FIGS. 4 through 6D correspond in principle to those according to FIGS. 1 through 3D. Corresponding parts, therefore, have been given the same reference numerals. The difference in these cases lie in the fact that the external thread 14 in FIG. 1A, for example, has been replaced by an internal thread, which is designated by reference numeral 21 in FIG. 4A. In the same manner, the internal thread 14' in FIGS. 2B though 2D is replaced by an external thread 21' in FIGS. 5B through 5D. The internal thread 21 may be continuous, as shown schematically in FIG. 4A. Preferably, however, it is broken up, and presented by a number of axially extending ridges 22, as shown in FIG. 7. As is also clearly evident from FIGS. 6A through 6D, each of the coupling components according to FIGS. 5A through 5D fit he nipple 6, as shown in FIG. 4A. A further detailed description of FIGS. 4 through 7 is therefore not required.

The present invention is not limited solely to the examples of embodiments described above, but can be varied within the framework of the following claims. For example, the groove 7 in the nipple 6 may be given many different designs, either as one recess or as a number of recesses.

I claim:

1. A nipple for use in coupling to a plurality of secondary coupling components, said nipple comprising a longitudinally extending hollow cylindrical member having an inner surface, an outer surface, an inner end and a outer end, said outer surface of said longitudinally extending hollow cylindrical member including an outer recess adapted for engagement with a secondary coupling component including locking means for telescopingly engaging said outer recess, said nipple including thread means located on said inner surface of said longitudinally extending hollow cylindrical member between said outer recess and said outer end of said longitudinally extending hollow cylindrical member, said thread means adapted for engagement with a threaded secondary coupling component including corresponding threads thereon, and said thread means comprising a plurality of axially extending bead components, said bead components being adapted to interact with an internal valve in said secondary coupling component.

2. The nipple of claim 1 wherein said outer recess comprises an annular groove extending about the outer periphery of said longitudinally extending hollow cylindrical member.

3. The nipple of claim 1 wherein said plurality of bead components comprise three such bead components evenly distributed about said inner surface of said longitudinally extending hollow cylindrical member.

4. The nipple of claim 1 wherein said thread means is separated from said outer recess on said outer surface of said longitudinally extending hollow cylindrical member.

5. Apparatus for diffusion or filtration including at least one nipple, said nipple being adapted for use in coupling said apparatus to a plurality of secondary coupling components, said nipple including a longitudinally extending hollow cylindrical member having an inner surface, an outer surface, an inner end and an outer end, and said outer surface of said longitudinally extending hollow cylindrical member including an outer recess adapted for engagement with a secondary coupling compnent including locking means for telescopingly engaging said outer recess, said nipple including thread means located on said inner surface of said longitudinally extending hollow cylindrical members located between said recess and said outer end of said longitudinally extending hollow cylindrical member and being adapted for engagement with a threaded secondary coupling component including corresponding threads thereon, said thread means comprising a plurality of axially extending bead components, said bead components being adapted to interact with an internal valve in aid secondary coupling component.

6. The apparatus of claim 5, wherein said outer recess comprises an annular groove extending about the outer periphery of said longitudinally extending hollow cylindrical member.

7. The apparatus of claim 5, wherein said plurality of bead components comprise three such bead components evenly distributed about said inner surface of said longitudinally extending hollow cylindrical member.

8. Apparatus for diffusion or filtration comprising a casing having a first inlet and a first outlet for a first fluid and a second inlet and a second outlet for a second fluid, at least one of said first inlet and first outlet comprising a nipple integral with said casing, said nipple being adapted for use in coupling said apparatus to a plurality of secondary coupling components including at least one first secondary coupling component designed for single usage and at least one second secondary coupling component designed for reuse, whereby said first fluid can be passed through said at least one of said first inlet and first outlet, said nipple including a longitudinally extending hollow cylindrical member having an inner surface, an outer surface, an inner end and an outer end, and said outer surface of said longitudinally extending hollow cylindrical member including an outer recess adapted for engagement with said at least one second secondary coupling component comprising a secondary coupling component for telescopingly engaging said outer surface of said longitudinally extending hollow cylindrical member and including locking means for engaging said outer recess, said nipple including thread means located between said recess and said outer end of said longitudinally extending hollow cylindrical member and being adapted for engagement with said at least one first secondary coupling component comprising a threaded secondary coupling component including corresponding threads thereon.

9. The apparatus of claim 8 wherein said thread means are located on said outer surface of said longitudinally extending hollow cylindrical member.

10. The apparatus of claim 8 wherein said thread means are located on said inner surface of said longitudinally extending hollow cylindrical member.

11. The apparatus of claim 8 wherein said outer recess comprises an annular groove extending about the outer periphery of said longitudinally extending hollow cylindrical member.

12. The apparatus of claim 11 wherein said thread means are located on said outer surface of said longitudinally extending hollow cylindrical member, and wherein said longitudinally extending hollow cylindrical member includes a raised cylindrical portion located between said annular groove and said outer end of said longitudinally extending hollow cylindrical member.

13. The apparatus of claim 12 wherein said raised cylindrical portion is adapted to serve as a sealing surface with respect to at least one of said plurality of secondary coupling components.

14. The apparatus of claim 12 including a chamfered surface located between said raised cylindrical portion and said outer end of said longitudinally extending hollow cylindrical member, said chamfered surface adapted to act as a seal with respect to at least one of said plurality of secondary coupling components.

15. The apparatus of claim 14 wherein said raised cylindrical portion has a first diameter, and wherein said outer end of said longitudinally extending cylindrical member include an end cylindrical portion having a second diameter, said second diameter being less than said first diameter.

16. The apparatus of claim 9 wherein said thread means is dimensioned such that said thread means are not engageable with said locking means of said at least one second secondary coupling component.

17. The apparatus of claim 15 wherein said thread means has a predetermined depth so as to provide an internal thread diameter for said thread means, and wherein said second diameter is less than said internal thread diameter.

18. The apparatus of claim 10 wherein said thread means comprises a plurality of axially extending bead components, said bead components being adapted to interact with an internal valve in said at least one second secondary coupling component.

19. The apparatus of claim 18 wherein said plurality of bead components comprise three such bead components evenly distributed about said inner surface of said longitudinally extending hollow cylindrical member.

20. The apparatus of claim 8 wherein said thread means is separated from said outer recess on said outer surface of said longitudinally extending hollow cylindrical member.

21. Apparatus for diffusion or filtration comprising a casing, and at least one nipple integrally connected to a portion of said casing, said nipple being adapted for use in coupling said apparatus to a plurality of secondary coupling components including at least one first secondary coupling component designed for single usage and at least one second secondary coupling component designed for reuse, said nipple including a longitudinally extending hollow cylindrical member having an inner surface, an outer surface an inner end and an outer end, and said outer surface of said longitudinally extending hollow cylindrical member including an outer recess comprising an annular groove extending about the outer periphery of said longitudinally extending hollow cylindrical member, said annular groove adapted for engagement with said at least one second secondary coupling component comprising a secondary coupling component telescopingly engageable with said outer surface of said longitudinally extending hollow cylindrical member and including locking means for engaging said annular groove, said longitudinally extending hollow cylindrical member including a raised cylindrical portion located between said annular groove and said outer end of said longitudinally extending hollow cylindrical member, said raised cylindrical portion being adapted to serve as a sealing surface with respect to at least one of said secondary coupling components, said nipple including thread means located on the outer surface of said longitudinally extending hollow cylindrical member between said recess and said outer end of said longitudinally extending hollow cylindrical member and being adapted for engagement with said at least one first secondary coupling component comprising a threaded secondary component including corresponding threads thereon.

22. Apparatus for diffusion or filtration comprising a casing, and at least one nipple integrally connected to a portion of said casing, said nipple being adapted for use in coupling said apparatus to a plurality of secondary coupling components including at least one first secondary coupling component designed for single usage and at least one second secondary coupling component designed for reuse, said nipple including a longitudinally extending hollow cylindrical member having an inner surface, an outer surface, an inner end and an outer end, said outer surface of said longitudinally extending hollow cylindrical member including an outer recess comprising an annular groove extending about the outer periphery of said longitudinally extending hollow cylindrical member, and adapted for engagement with said at least one second secondary coupling component comprising a secondary coupling component which is telescopingly engageable with said outer surface of said longitudinally extending hollow cylindrical member and which includes locking means for engaging said outer recess, said longitudinally extending hollow cylindrical member including a raised cylindrical portion located between said annular groove and said outer end of said longitudinally extending hollow cylindrical member, said nipple including thread means located on said outer surface of said longitudinally extending hollow cylindrical member between said recess and said outer end of said longitudinally extending hollow cylindrical member and being adapted for engagement with said at least one first secondary coupling component comprising a threaded secondary coupling component including corresponding threads thereon, and including a chamfered surface located between said raised cylindrical portion and said outer end of said longitudinally extending hollow cylindrical member, said chamfered surface adapted to act as a seal with respect to at least one of said plurality of secondary coupling components.

23. The apparatus of claim 22 wherein said raised cylindrical portion has a first diameter, and wherein said outer end of said longitudinally extending cylindrical member includes an end cylindrical portion having a second diameter, said second diameter being less than said first diameter.

24. The apparatus of claim 23 wherein said thread means has a predetermined depth so as to provide an internal thread diameter for said thread means, and wherein said second diameter is less than said internal thread diameter.

25. The apparatus of claim 21 or 22 wherein said thread means is separated from said outer recess on said outer surface of said longitudinally extending hollow cylindrical member.

* * * * *

UNITED STATES PATENT AND TRADEMARK OFFICE
CERTIFICATE OF CORRECTION

PATENT NO. : 5,165,728
DATED : November 24, 1992
INVENTOR(S) : Georg Mayer

It is certified that error appears in the above-identified patent and that said Letters Patent is hereby corrected as shown below:

Column 6, line 23, delete "he" and insert therefor --the--.
Column 7, line 17, delete "aid" and insert therefor --said--.
Column 8, line 16, "include" should read --includes--.
Column 8, line 50, following "surface" (second occurrence), insert --,--.

Signed and Sealed this

Twelfth Day of October, 1993

BRUCE LEHMAN

Attest:

Attesting Officer

Commissioner of Patents and Trademarks